United States Patent
Latino et al.

(10) Patent No.: US 9,042,425 B2
(45) Date of Patent: May 26, 2015

(54) VACUUM CLEANING STRUCTURE FOR ELECTRODE FURNACE

(75) Inventors: Octavio R. Latino, Berrien Springs, MI (US); Gordon C. Ford, St. Joseph, MI (US); Lloyd A. Allen, St. Joseph, MI (US)

(73) Assignee: Leco Corporation, St. Joseph, MI (US)

( * ) Notice: Subject to any disclaimer, the term of this patent is extended or adjusted under 35 U.S.C. 154(b) by 571 days.

(21) Appl. No.: 13/358,096

(22) Filed: Jan. 25, 2012

(65) Prior Publication Data

US 2012/0213244 A1 Aug. 23, 2012

Related U.S. Application Data

(60) Provisional application No. 61/444,294, filed on Feb. 18, 2011.

(51) Int. Cl.
*H05B 3/62* (2006.01)
*H05B 3/48* (2006.01)
*G01N 21/00* (2006.01)

(52) U.S. Cl.
CPC ........................................ *H05B 3/62* (2013.01)

(58) Field of Classification Search
CPC . H01J 49/0468; G01N 1/4022; G01N 33/206; G01N 35/04; G01N 2035/0463; G01N 2035/0406; G01N 2035/0427; H05B 3/0014; H05B 3/62; H05B 3/06; B01L 3/04; F27D 11/02; F27D 2019/0003
USPC ......... 373/109, 110, 111, 112, 115, 116, 117, 373/119, 120, 121, 122, 123, 124, 125, 126, 373/127, 128, 129, 130, 131, 132, 133, 134, 373/135, 136, 137; 422/62, 63, 64, 65, 93
See application file for complete search history.

(56) References Cited

U.S. PATENT DOCUMENTS

| | | | | |
|---|---|---|---|---|
| 3,342,250 | A | * | 9/1967 | Treppschuh et al. ......... 164/469 |
| 3,448,972 | A | * | 6/1969 | Derham ........................ 422/109 |
| 3,899,627 | A | * | 8/1975 | Sitek et al. .................... 373/118 |
| 3,936,587 | A | | 2/1976 | Sitek et al. |
| 3,946,228 | A | * | 3/1976 | Biermann ..................... 250/282 |
| 4,028,076 | A | * | 6/1977 | Fields ............................. 55/394 |
| 4,056,677 | A | * | 11/1977 | Berk et al. ..................... 373/118 |
| 4,234,541 | A | | 11/1980 | Bredeweg et al. |
| 4,328,386 | A | | 5/1982 | Bredeweg |
| 4,371,971 | A | * | 2/1983 | Bredeweg ..................... 373/115 |
| 4,388,722 | A | * | 6/1983 | Tanimoto ..................... 373/118 |
| 4,404,461 | A | * | 9/1983 | Sitek et al. .................... 219/490 |
| 4,419,754 | A | | 12/1983 | Sitek et al. |
| 4,428,161 | A | * | 1/1984 | Walther et al. ................ 451/327 |
| 4,510,610 | A | * | 4/1985 | Hosokawa et al. ........... 373/118 |
| 4,919,191 | A | * | 4/1990 | Brodersen ..................... 164/495 |
| 4,969,934 | A | * | 11/1990 | Kusik et al. .................... 95/270 |

(Continued)

*Primary Examiner* — Dana Ross
*Assistant Examiner* — Gyounghyun Bae
(74) *Attorney, Agent, or Firm* — Price Heneveld LLP

(57) ABSTRACT

An electrode for a resistance analytical furnace has a crucible-engaging surface and an end spaced from the crucible-engaging surface having a plurality of grooves formed therein. A manifold mounted on the end of the electrode defines a dust recovery plenum and includes an outlet communicating with the plenum for coupling to a vacuum source to remove debris from the electrode. The improved electrode and electrode cleaning manifold positioned on the electrode provides a turbulent airflow for removal of dust and debris from an analytical furnace.

24 Claims, 14 Drawing Sheets

(56) References Cited

U.S. PATENT DOCUMENTS

| | | | | |
|---|---|---|---|---|
| 5,593,043 A * | 1/1997 | Ozmerih | | 209/303 |
| 5,789,910 A * | 8/1998 | Guthrie | | 324/71.4 |
| 6,291,802 B1 * | 9/2001 | Ford | | 219/427 |
| 7,077,885 B2 * | 7/2006 | Charlat | | 95/52 |
| 7,402,280 B2 * | 7/2008 | Ford | | 422/63 |
| 2003/0175156 A1 * | 9/2003 | Ford | | 422/63 |
| 2003/0197125 A1 * | 10/2003 | De Saro et al. | | 250/339.07 |
| 2009/0321223 A1 * | 12/2009 | Hirata et al. | | 198/562 |

\* cited by examiner

VACUUM CLEANING STRUCTURE FOR ELECTRODE FURNACE

CROSS-REFERENCE TO RELATED APPLICATIONS

This application claims priority under 35 U.S.C. §119(e) and the benefit of U.S. Provisional Application No. 61/444,294, entitled VACUUM CLEANING INTERFACE FOR ELECTRODE FURNACE, filed on Feb. 18, 2011, by Octavio R. Latino, et al., the entire disclosure of which is incorporated herein by reference.

BACKGROUND OF THE INVENTION

The present invention relates to analytical furnaces and particularly to an improved electrode and vacuum system for cleaning the electrodes and furnace area of a resistance furnace.

Analytical furnaces heat specimens, such as chips and pin samples, and the like, typically ranging in mass of about 1 gram or less in a crucible. Resistance furnaces employ graphite crucibles clamped between two electrodes which pass an electrical current through the crucible, heating specimens to temperatures of 2500° C. or higher. The gaseous byproducts of fusing the specimen are then swept by an inert gas through the furnace system to an analyzer for the subsequent analysis of the specimen gases of interest using suitable detectors. Such an analyzer is represented by Model TCH600 commercially available from Leco Corporation of St. Joseph, Mich.

During the heating of a specimen, the enclosed furnace chamber becomes contaminated with debris, dust, soot, and the like from the byproducts of fusing the sample and needs to be frequently cleaned. In the past, between cycles of analysis, a vacuum was supplied to the general area of the electrodes for removing such dust and debris. Also, a powered rotary brush has been employed in the furnace area of a resistance furnace to remove debris from the electrodes. Although such a system has been relatively successful, with the increased sensitivity of detectors and the ability to measure lower levels of analytes, there remains a need to more frequently clean the furnace as well as improve the cleaning of analytical furnaces between analyses.

SUMMARY OF THE INVENTION

The system of this invention provides an improved electrode and electrode cleaning manifold which is positioned on the electrode to increase the airflow turbulence for removal of dust and debris during cleaning of an analytical furnace. One embodiment of the invention is an electrode for engaging a crucible, which electrode has an end spaced from the crucible-engaging surface with a plurality of grooves formed therein, allowing cleaning air to flow through the grooves. In another embodiment, a manifold for fitting over the end of the electrode is provided to provide a dust recovery plenum. An outlet communicating with the plenum is coupled to a vacuum source to remove debris from the furnace and electrode. Systems embodying the present invention include an electrode having an end with a plurality of curved grooves formed therein and a manifold, which fits over the end of the electrode. The manifold defines a dust recovery plenum coupled to an outlet for coupling to a vacuum source to remove debris from the furnace and electrode. In a further embodiment, the system also includes an abrading brush used concurrently with the dust removing vacuum source.

With these improvements, the analytical furnace can be frequently cleaned and the quality of cleaning improved.

These and other features, objects and advantages of the present invention will become apparent upon reading the following description thereof together with reference to the accompanying drawings.

DETAILED DESCRIPTION OF THE PREFERRED EMBODIMENT

Figure 1:
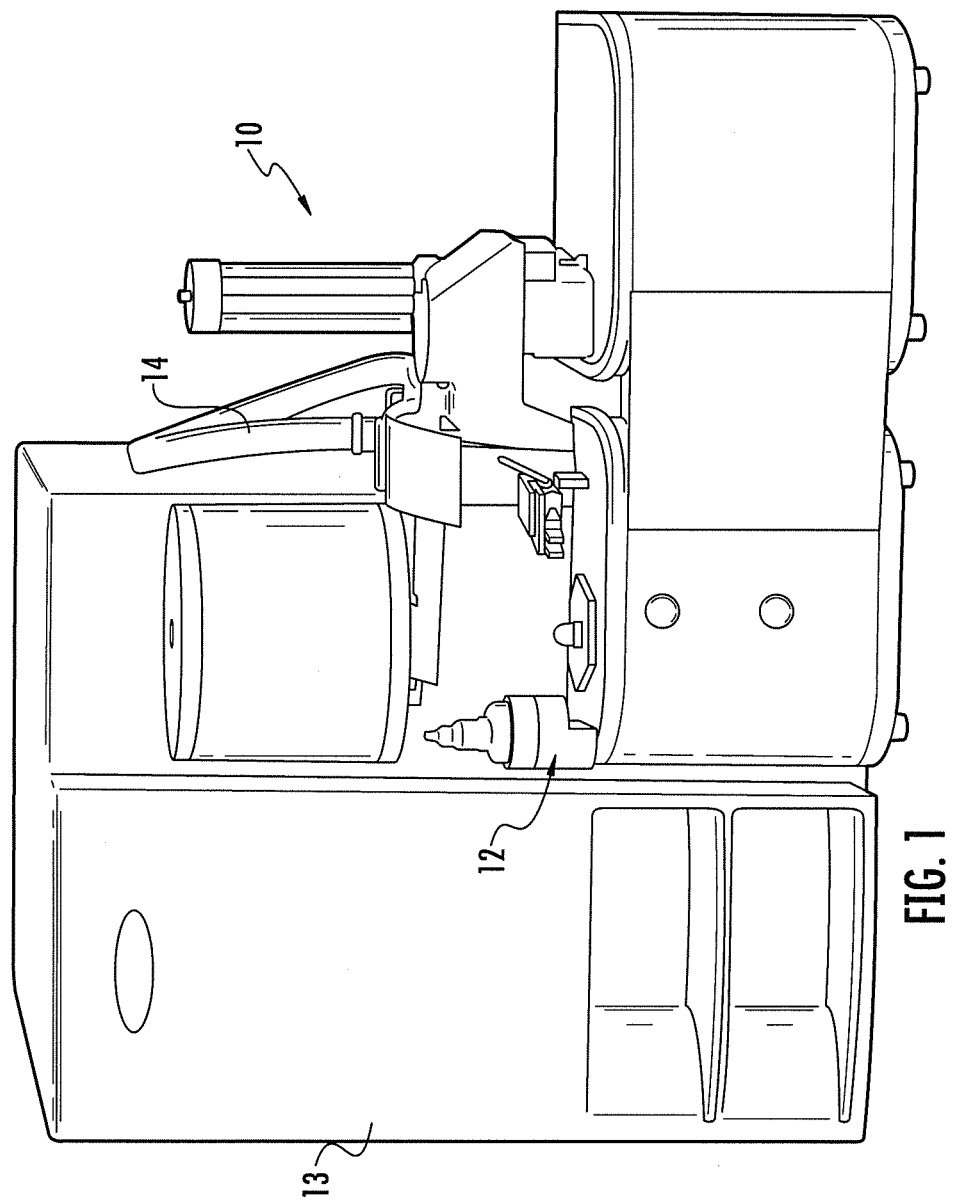
FIG. 1 is front perspective view of an analyzer including a fusion furnace having the improved electrode cleaning system of the present invention.
Figure 2:
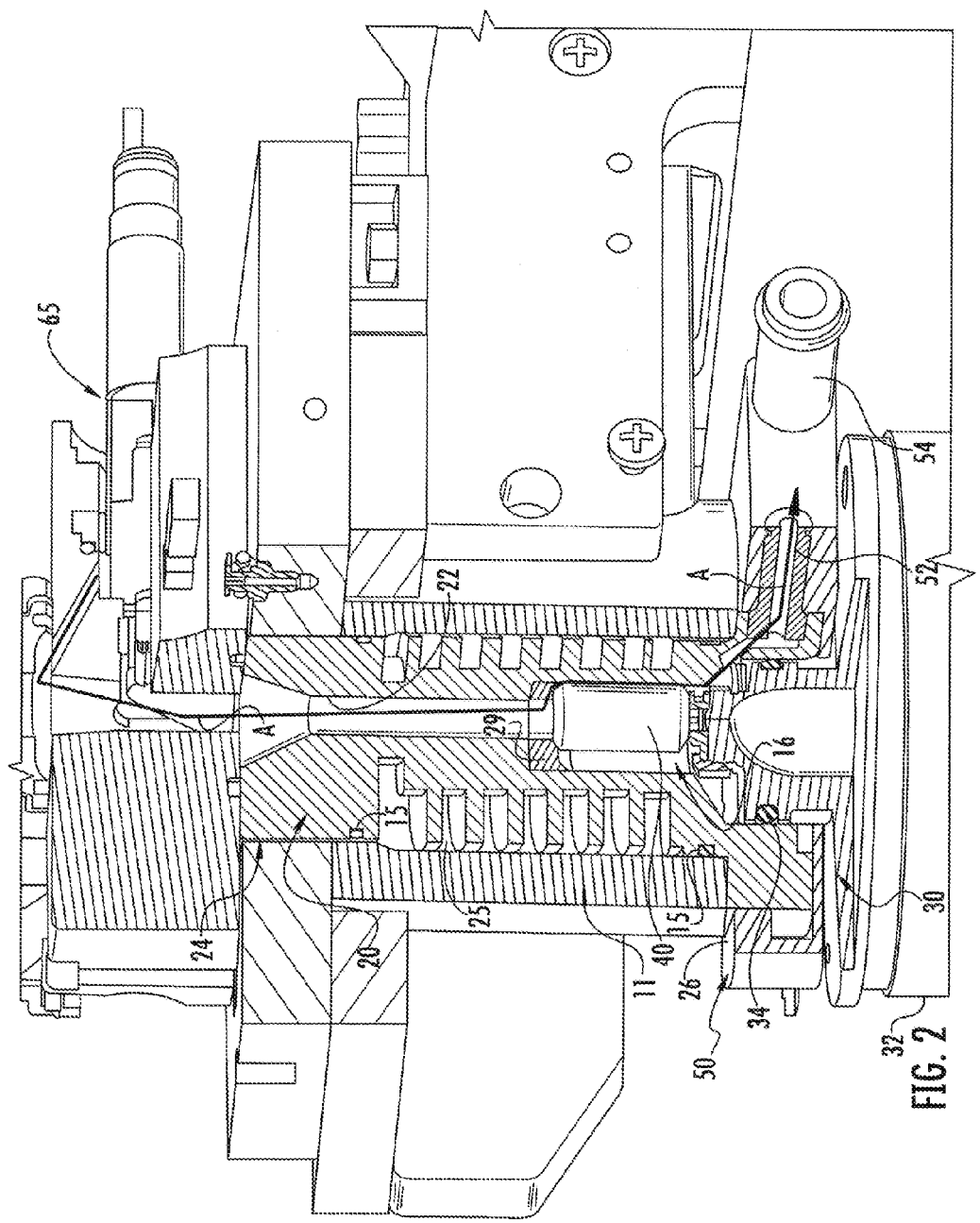
FIG. 2 is a fragmentary cross-sectional view of the furnace for an instrument as shown in FIG. 1, showing a crucible in place during a fusion cycle.

Referring initially to FIG. 1, there is shown an analytical instrument 10, such as a Model ONH836 nitrogen, oxygen, hydrogen analyzer, commercially available from Leco Corporation of St. Joseph, Mich. The instrument is designed to incorporate the present invention and includes a resistance furnace 16, as best seen in FIG. 2. The furnace includes an upper electrode 20 incorporating one aspect of the present invention and a lower electrode 30 which sealably encloses the furnace chamber within the upper electrode and engages a graphite crucible 40 positioned between the upper and lower electrodes. A suitable power supply is conventionally coupled to the upper and lower electrodes to pass sufficient current through crucible 40 to heat a sample specimen contained therein to a temperature of 2500° C. or higher to release analyte gases from the sample. As is well known, a supply of inert carrier gas, such as helium, flows downwardly through the central opening 22 of upper electrode 20 in the direction indicated by the flow path identified by arrow A into the mouth of the crucible and exits the chamber through a gas outlet port 52 in electrode 20. Port 52 is a cylindrical tube which extends through manifold 50 embodying one aspect of the present invention and supplies the flow of inert gas and analyte in a conventional flow path to the analyzer 13 (FIG. 1) for analysis.

Figure 5:
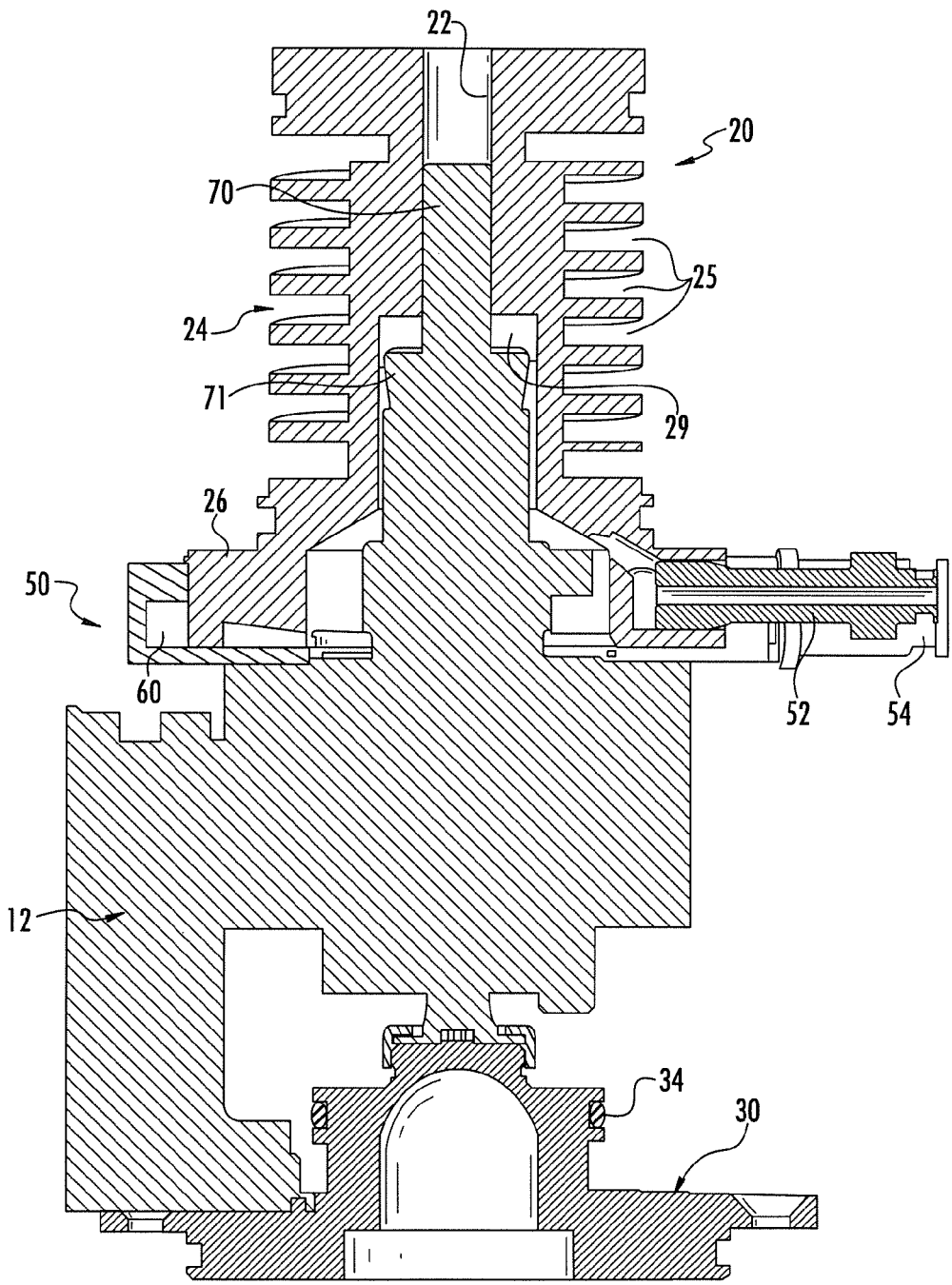
FIG. 5 is a vertical cross-sectional view of the upper electrode, manifold, and lower electrode in an open position with the electrode brush cleaner in a use position.

The lower electrode 30 is raised and lowered in a conventional manner by a movable pedestal 32 coupled to an actuating cylinder (not shown) which raises it into a position for heating of the sample, as shown in FIG. 2, and lowers the lower electrode 30, as shown in FIG. 5, to allow an automatic cleaning brush assembly 12 (FIGS. 1, 5, 13, and 14) to move into position for brushing the interior of the furnace 16, including surfaces of members 22 and 29 of the upper electrode as an optional cleaning step. With the improved cleaning airflow provided by the upper electrode design and manifold, some cleaning cycles can eliminate the brushing step provided by assembly 12 and use only the vacuum cleaning, thus, greatly reducing the time between successive analyses. Typically, however, the upper electrode is also cleaned by the rotary brush 70 (FIG. 14) with the loose debris being removed through vacuum line 14 coupled to vacuum manifold outlet 54. The unique design of electrode 20 and manifold 50 provides a highly improved flow rate and turbulence of air through the furnace 16 to sweep the loosened debris from the furnace. Before describing the interrelationship of the upper electrode 20 and manifold 50 to achieve this aspect of the invention, a description of each of these elements is presented.

Figure 3:
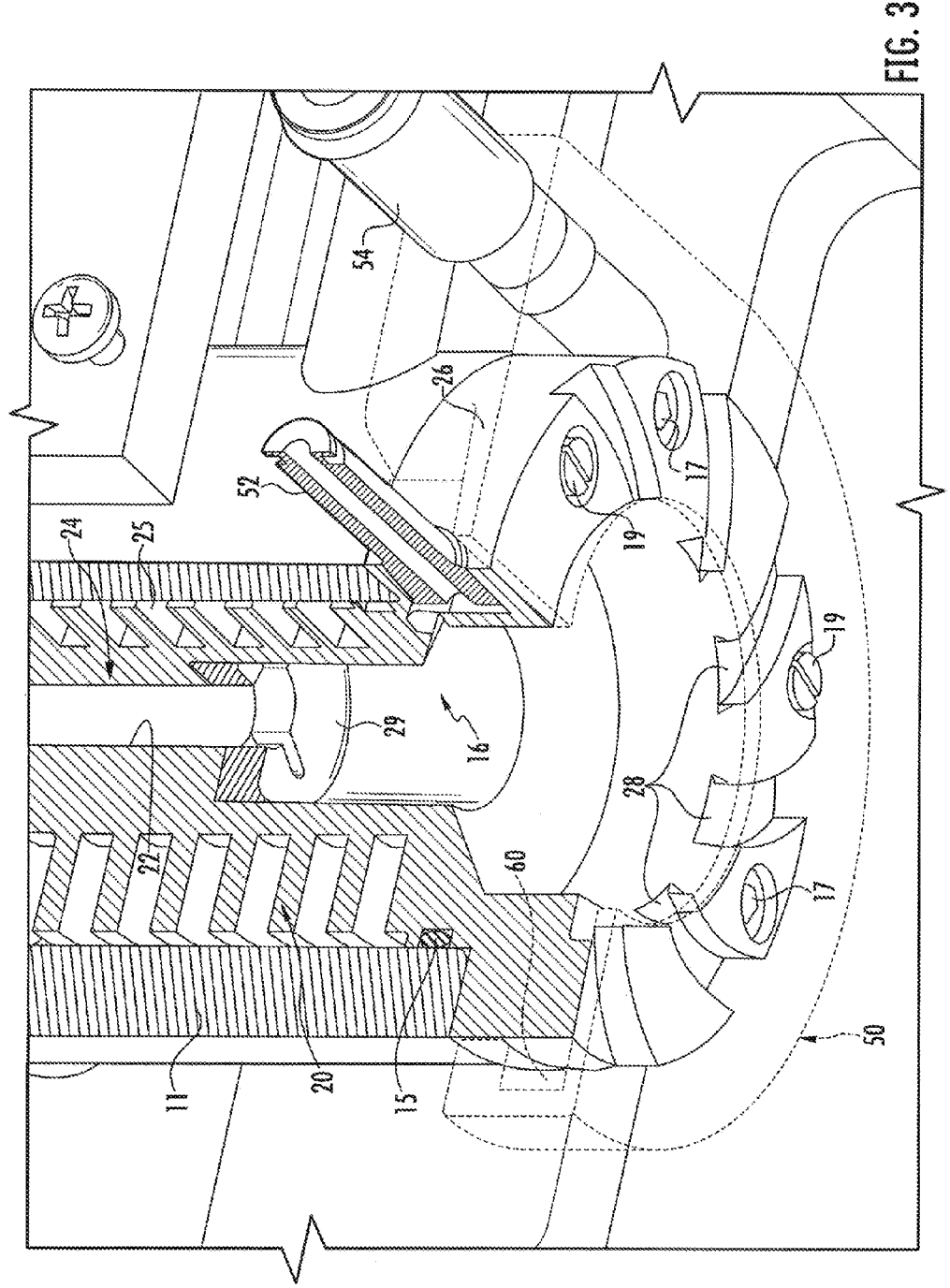
FIG. 3 is a bottom perspective cut-away view, partly in phantom, of the upper furnace electrode and cleaning manifold attached thereto.
Figure 4:
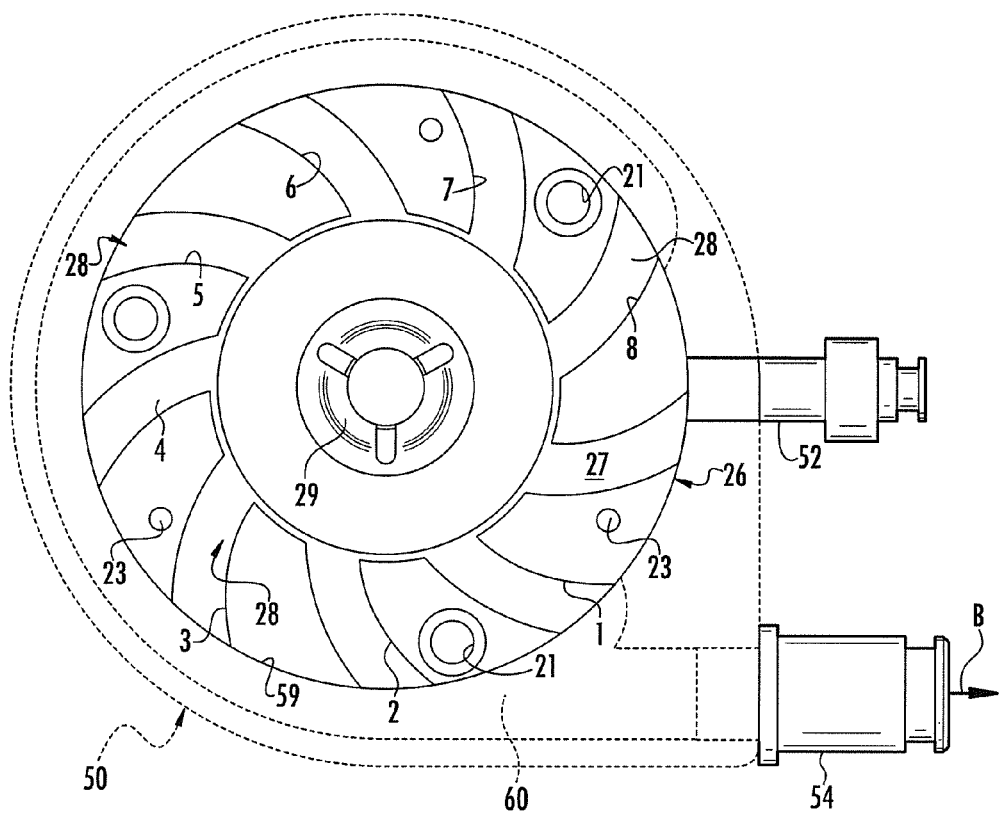
FIG. 4 is a bottom plan view of the upper electrode and manifold partly shown in phantom.

Referring initially to the upper electrode construction shown in FIGS. 2-4, 6, 8 and 9, the upper electrode 20 has a generally cylindrical body 24 with groove 25 formed therein for cooling when sealed in cooling chamber 11 (FIGS. 2 and 3) by upper and lower O-rings 15. The upper electrode includes a central, generally cylindrical passageway 22 for receiving a sample from a sample drop assembly 65, which can be of the type disclosed in U.S. Pat. No. 6,291,802, entitled SAMPLE INTRODUCTION ASSEMBLY, the disclosure of which is incorporated herein by reference. Passageway 22 is generally cylindrical and extends along the axis of the cylindrical body 24 for the passage of an inert carrier gas, such as helium, as seen by arrow A in FIG. 2. The lower end of the cylindrical passageway 22 enlarges in diameter to define the cylindrical crucible-receiving furnace 16. Electrode 20 includes a lower flange 26 with apertures 21 (FIGS. 4 and 8) for mounting the electrode to the cooling chamber 11 of the furnace 16 utilizing conventional fasteners 17 (FIG. 3). Flange 26 also includes apertures 23 for securing manifold 50 to the flange 26, as shown in FIGS. 3, 6, 7, and 12, using conventional fasteners 19 (FIG. 3). Gas outlet port 52 extends through a slot 51 (FIGS. 11 and 12) in manifold 50 and communicates with the furnace 16 and passageway 22 in upper electrode 20 for allowing the analyte and carrier gas to exit through the port 52, as shown by arrow A in FIG. 2, and into the analyzer instrument 13 (FIG. 1).

Figure 13:
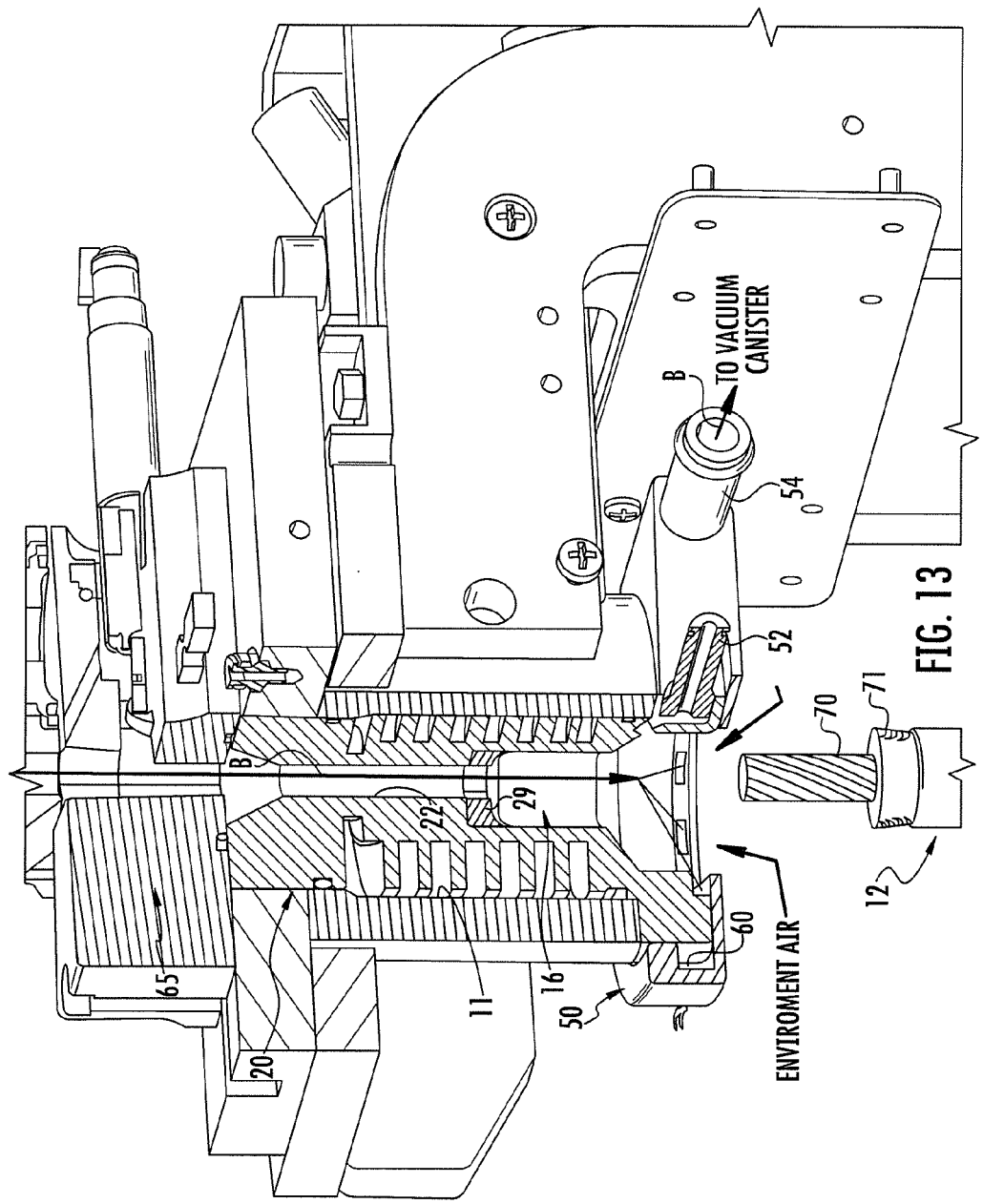
FIG. 13 is a vertical cross-sectional view of the furnace and a cleaning brush mechanism shown partially raised into the furnace and showing the cleaning airflow path.
Figure 14:
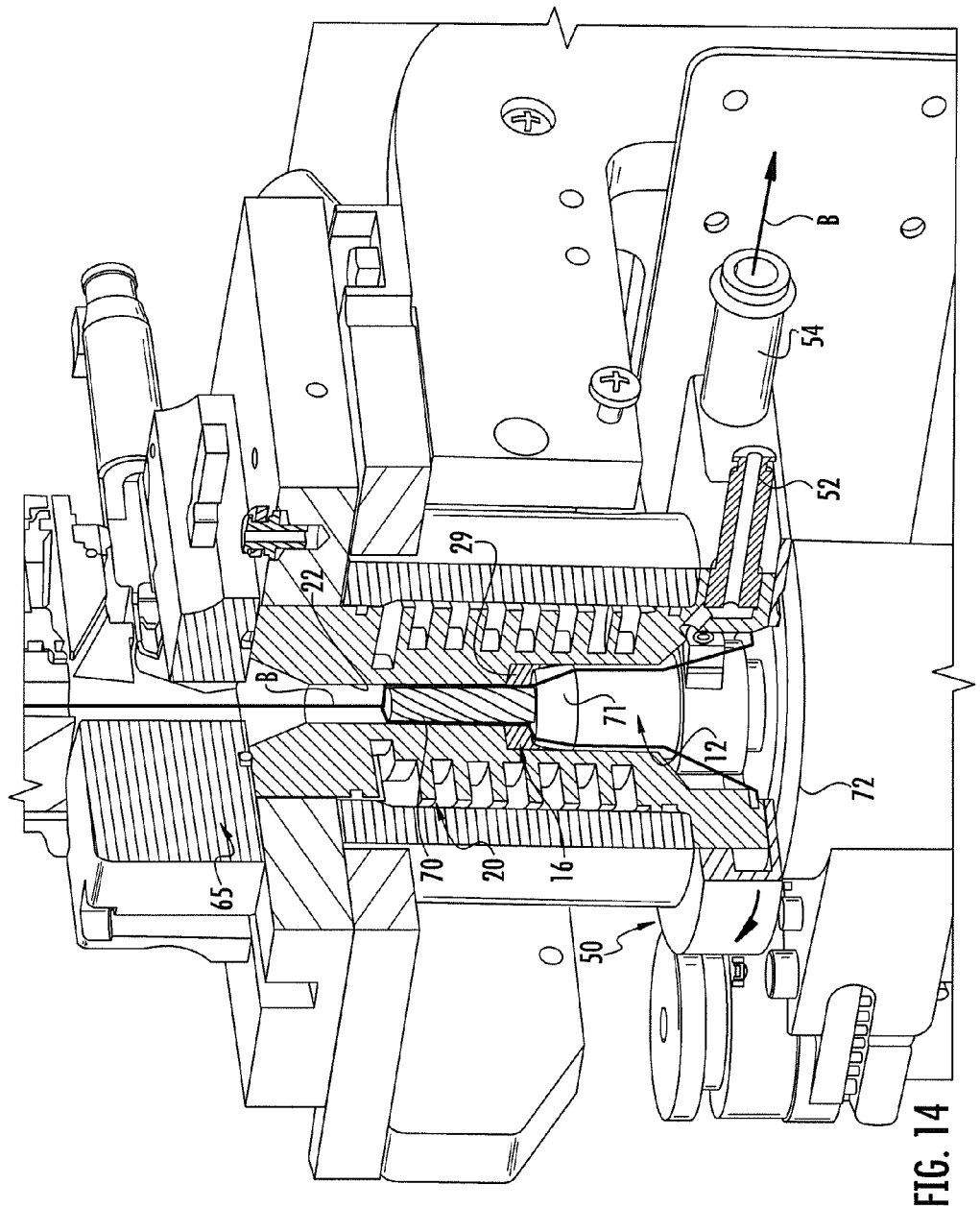
FIG. 14 is a cross-sectional view of the furnace shown with the cleaning brush fully engaged with the upper electrode.

Flange 26 includes a lower surface 27 (FIGS. 4 and 8) into which a plurality of angularly spaced-apart (about 40°) curved helical grooves 28 are formed. In the embodiment shown, eight grooves numbered 1-8 (FIG. 8) are employed. Grooves 28 spiral radially outwardly and, together with manifold 50, provide a turbulent airflow path, as illustrated by arrow B in FIGS. 7, 13, and 14, for removing debris from the furnace 16 (FIGS. 6 and 7) defined, in part, by the interior space of the enlarged lower area of passageway 22 of upper electrode 20. The grooves 28 progressively increase in depth from their inner radius to the outer radius of flange 26 with the dimensions of one embodiment being illustrated in Table 1. These dimensions may be varied ±20% for different furnace designs. This helical design of the eight grooves 28 provides a turbulent airflow when the vacuum hose 14 is coupled to fitting 54 and the furnace is opened, as seen in FIGS. 5, 13 and 14, for the efficient removal of debris from the electrode area.

TABLE 1

Figure 8:
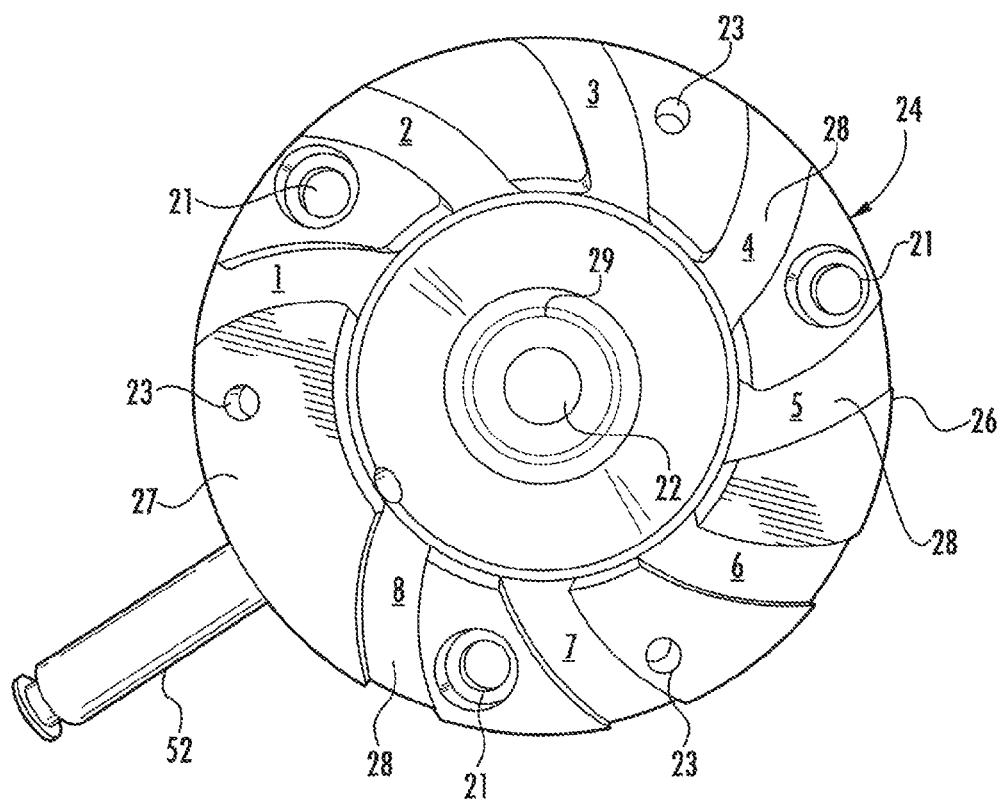
FIG. 8 is a bottom plan view of the end of the upper electrode.
Figure 9:
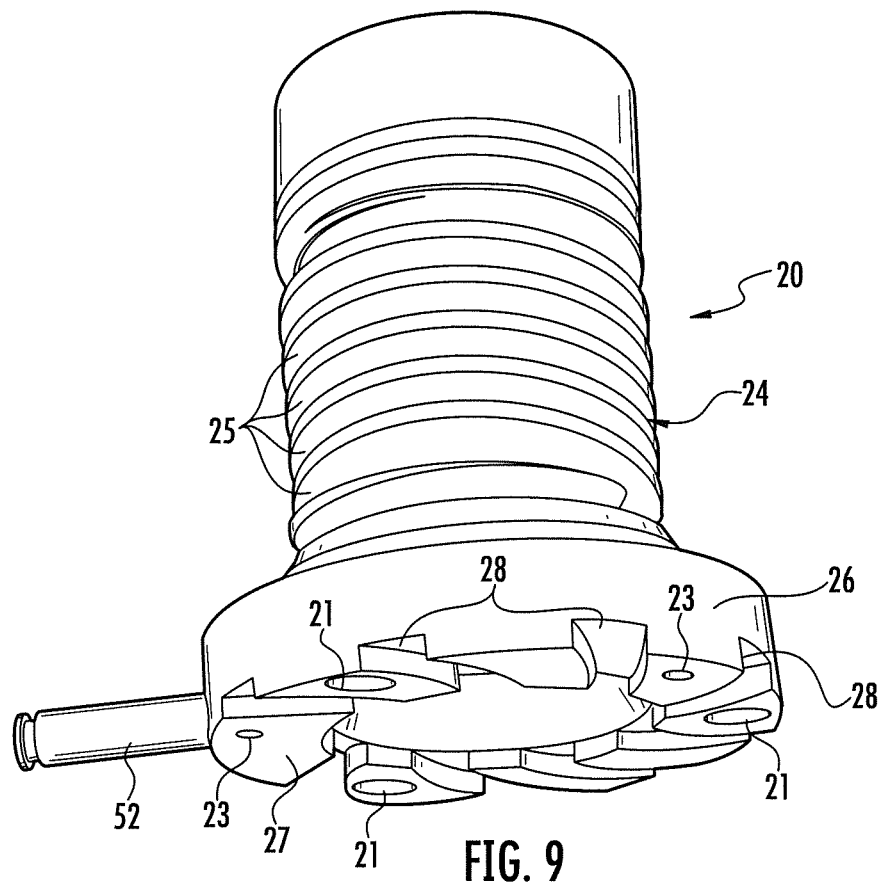
FIG. 9 is a perspective view of the upper electrode.

| GROOVE # | START DEPTH | END DEPTH |
| --- | --- | --- |
| FIG. 8: 1 | .100 inch | .100 inch |
| 2 | .100 inch | .125 inch |
| 3 | .100 inch | .150 inch |
| 4 | .100 inch | .175 inch |
| 5 | .100 inch | .200 inch |
| 6 | .100 inch | .225 inch |
| 7 | .100 inch | .250 inch |
| 8 | .100 inch | .275 inch |

The upper copper electrode includes a crucible-engaging contact, which is an annular tungsten-copper alloy insert 29 (FIGS. 2, 6, and 7) to provide wear resistance and durability for the electrode. Insert 29 contacts the upper annular surface of crucible 40, as illustrated in these figures. The lower electrode 30 is of conventional design employed in the past for the TCH600, including a tungsten-copper alloy crucible holder 36 (FIG. 6).

Figure 10:
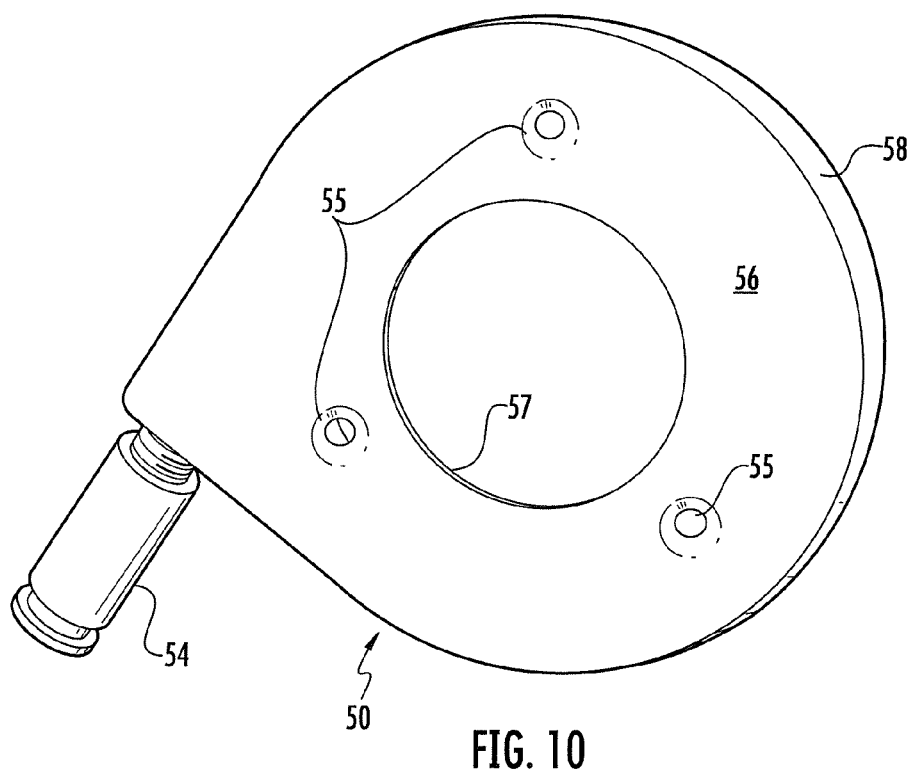
FIG. 10 is a bottom perspective view of the manifold which is mounted to the upper electrode.
Figure 11:
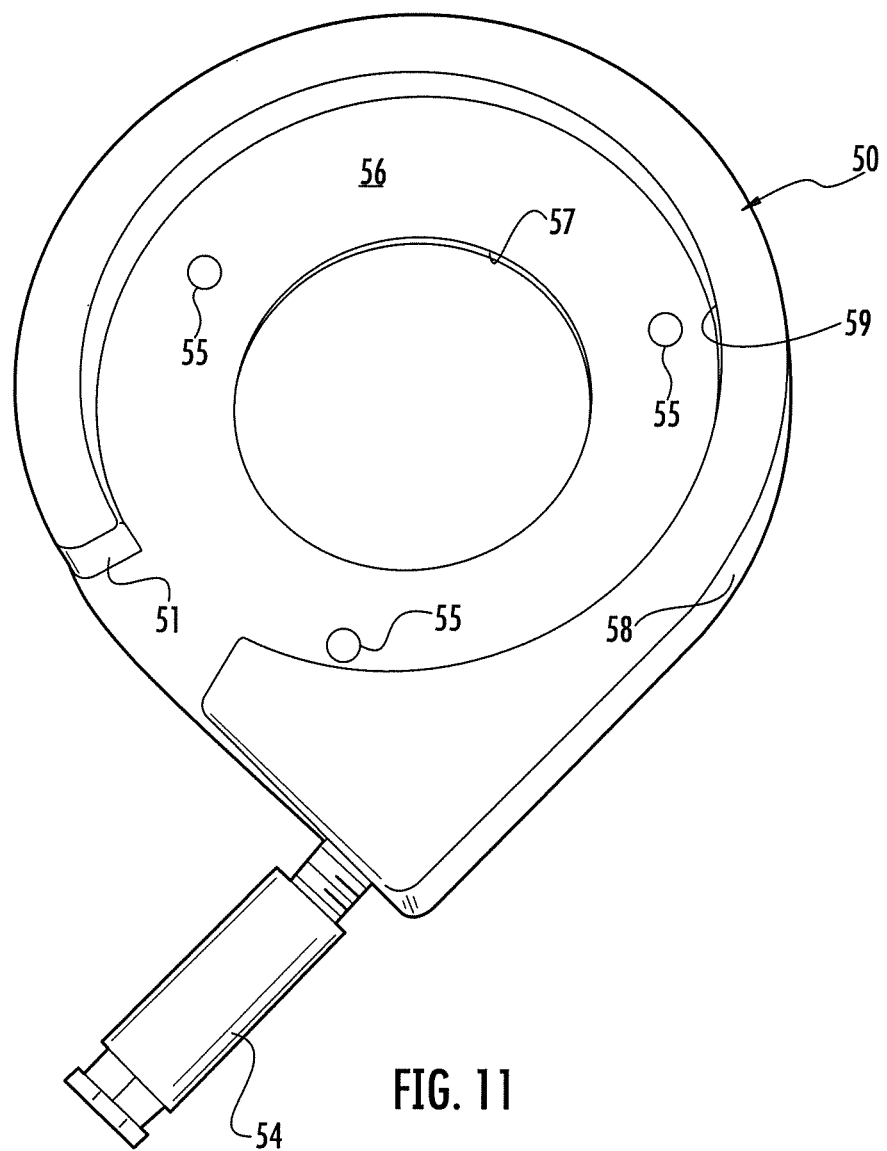
FIG. 11 is a top perspective view of the manifold.

The manifold 50, which is mounted to the upper electrode 20, can be integrally molded of a suitable polymeric material, such as polyether ether ketone (PEEK), and includes a vacuum outlet fitting 54 which is coupled to a vacuum source, such as vacuum hose 14 (FIG. 1), which, in turn, is coupled to a commercial canister-type vacuum cleaner (not shown) for providing sufficient airflow rate to withdraw dust and debris from the electrode area. Manifold 50, as best seen in FIGS. 10 and 11, has a generally annular floor 56 with apertures 55 aligned with apertures 23 in lower electrode flange 26. The inner surface of floor 56 (FIG. 11) is immediately adjacent and in contact with the outer surface 27 of flange 26 of upper electrode 20, as generally illustrated in the assembled view of FIGS. 7 and 12. The circular opening 57 in manifold 50 provides access for the lower electrode 30 to raise and lower a crucible 40 into and out of the furnace 16 of the upper electrode 20, as seen in FIGS. 6 and 7.

Vacuum outlet 54 communicates with and extends in tangential relationship to the annular plenum 60 (FIGS. 6 and 7) defined by the inner surface of the generally circular outer wall 58 of manifold 50 to improve the efficiency of the airflow drawn by the vacuum hose 14 through the furnace 16 during cleaning. The outer wall 58 of the manifold 50 terminates at its upper end in an inwardly extending lip 59, which extends in closely spaced relationship to the outer surface 31 of flange 26 of upper electrode 20, as illustrated in FIGS. 6 and 7. The annular space between the inner surface of generally circular wall 58 and between floor 56 and lip 59 defines an annular plenum 60 (FIGS. 3, 4, 6, and 7), which is generally rectangular and surrounds the flange 26 and communicates with grooves 28 in electrode 20. Plenum 60 communicates directly with the vacuum outlet 54. The manifold 50 includes a sealed off slot 51 through side wall 58 to allow the gas outlet port 52 from upper electrode 20 to extend therethrough, as seen in FIG. 12.

Figure 6:
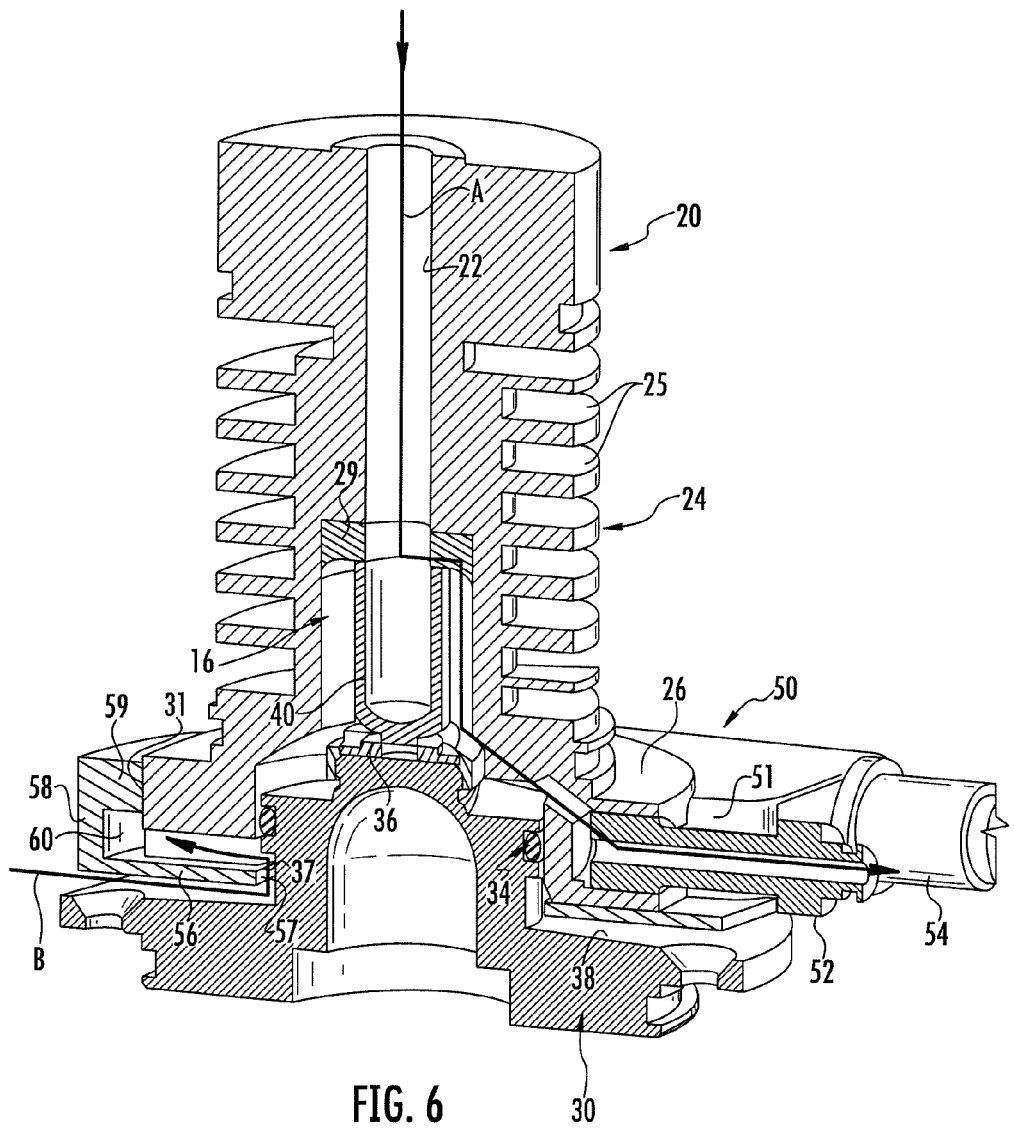
FIG. 6 is a vertical cross-sectional view of the upper electrode and lower electrode engaged for fusing a specimen in a crucible and showing the carrier gas flow path.
Figure 7:
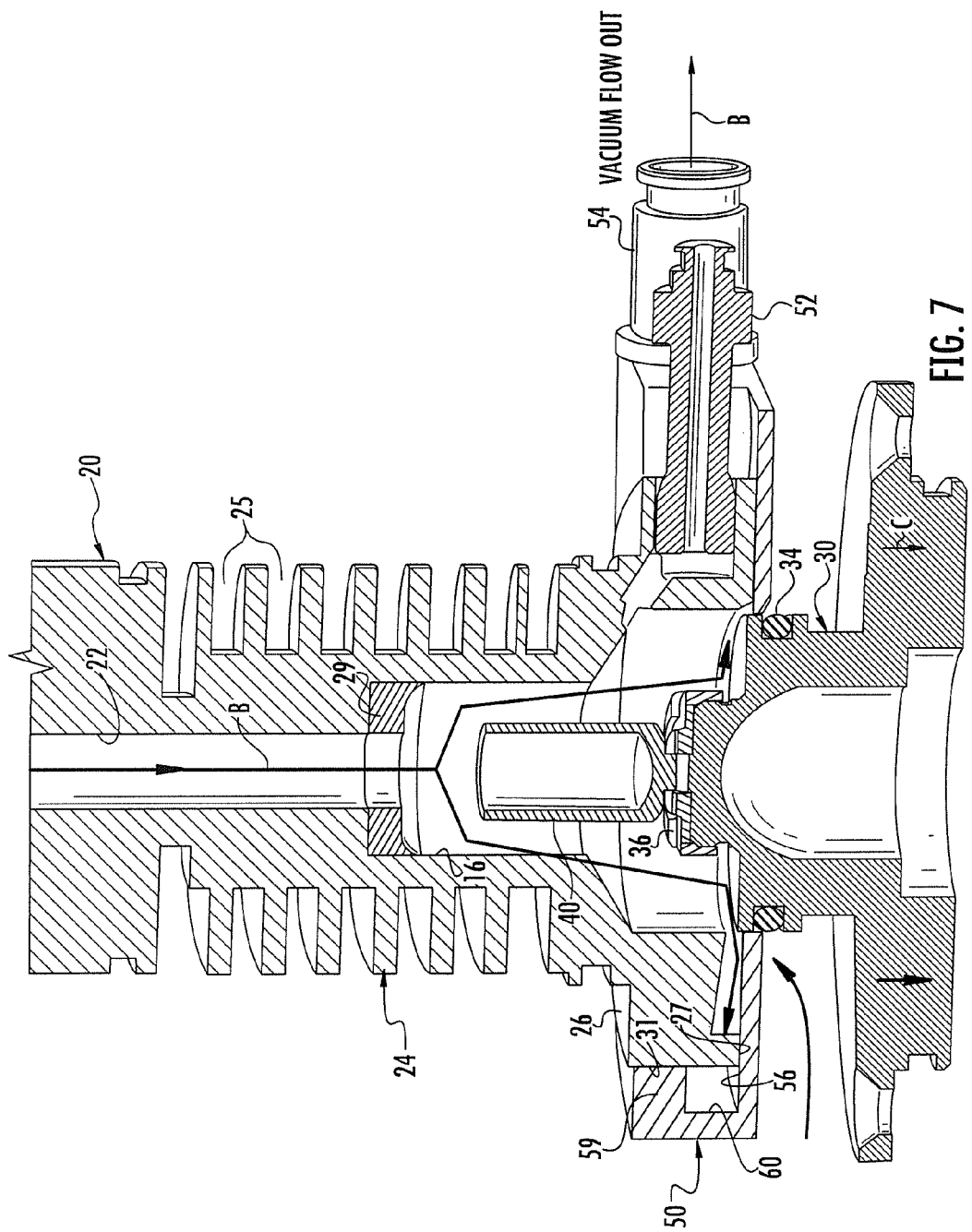
FIG. 7 is a vertical cross-sectional view of the structure shown in FIG. 6, showing the lower electrode being lowered and separated from the upper electrode during initiation of a cleaning cycle and showing the cleaning airflow path.

FIGS. 6 and 7 illustrate the flow paths of carrier gas and analyte during heating of a sample (arrow A) as well as during the vacuum cleaning cycle (arrow B), respectively. In FIG. 6, the lower electrode 30 is raised into a position in which its O-ring 34 seals the furnace 16 defined by the inner cylindrical walls of passageway 22 of upper electrode 20. In this position, the crucible 40 receives a supply of electrical current heating the crucible to indirectly heat a specimen. An inert carrier gas flows in the direction indicated by arrow A and removes the gaseous byproducts from a fused sample contained in the crucible 40 through the gas outlet port 52 formed in the electrode and extending through the slot 51 in manifold 50. In the position shown in FIG. 6, there exists a slight gap between the lower outer annular surface of floor 56 of manifold 50 and the upper annular surface 38 of lower electrode 30, allowing an airflow path, as shown by arrow B, between the larger diameter of opening 57 in the floor 56 and the smaller outer diameter of lower electrode in area 37 (FIG. 6). This allows air to flow into plenum 60 through grooves 28. This provides an airflow path through the vacuum outlet 54 when vacuum is applied to the hose 14 during heating of a sample.

Figure 12:
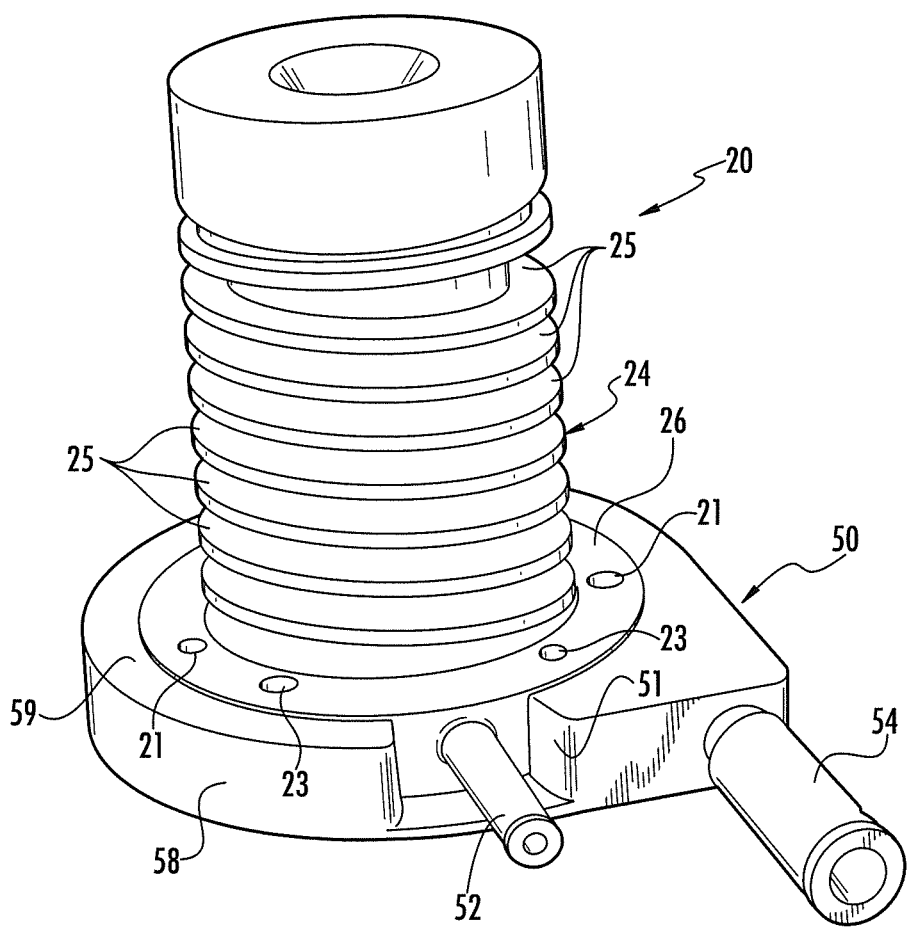
FIG. 12 is a perspective view of the upper electrode coupled to the manifold.

After fusion of the sample and analysis of the sample gas, the lower electrode is withdrawn, as illustrated in FIG. 7, lowering in a direction indicated by arrow C, and air is admitted through the top of the upper electrode and passageway 22, as indicated by arrow B in FIG. 12, to provide an abundance of airflow through the furnace 16 surrounding crucible 40. The air admitted through passageway 22 of electrode 20 is provided by opening the sealed slide block in conjunction with the gate valve in the sample drop assembly 65 (FIGS. 13 and 14) exposing passageway 22 to the atmosphere. Thus, as the lower electrode is initially moved from a totally sealed position (shown in FIG. 6) to a partially sealed position (shown in FIG. 7), a relatively high velocity spiral flow of air passes through the furnace 16 and grooves 28 in the upper electrode and into plenum 60. This flow exhausts through the vacuum outlet 54 removing dust and debris from the furnace and areas between the upper and lower electrodes.

In some models of the analyzer, a cleaning brush assembly 12 (FIG. 1) is employed and swings into position and is activated, as shown in FIGS. 13 and 14, to raise a stepped rotary brush 70 and abrader 71 into the furnace 16, as illustrated in FIG. 14, to mechanically abrade the inner surfaces of electrode 20 and insert 29 for removal of debris.

It will become apparent to those skilled in the art that various modifications to the preferred embodiment of the invention as described herein can be made without departing from the spirit or scope of the invention as defined by the appended claims.

The invention claimed is:

1. A dust recovery system for an electrode of an analytical resistance furnace comprising:
   an analytical furnace including a chamber for housing an upper electrode;
   an upper electrode positioned in said chamber and having a crucible-receiving furnace with a contact for engaging one end of a resistive crucible, said upper electrode having an end spaced from said contact with a plurality of grooves formed therein;
   a lower electrode for supporting an opposite end of a crucible within said furnace of said upper electrode; and
   a manifold fitted over said end of said upper electrode to define a dust recovery plenum surrounding said plurality of grooves in said upper electrode, said dust recovery plenum including an outlet for coupling to a vacuum source to remove debris from said electrode.

2. The system as defined in claim 1 wherein said grooves are curved.

3. The system as defined in claim 2 wherein said grooves are spiral.

4. The system as defined in claim 3 wherein said grooves increase in size in a radially outward direction.

5. The system as defined in claim 4 wherein said grooves extend tangentially to said plenum.

6. The system as defined in claim 1 wherein said manifold includes an annular floor which engages an end surface of said electrode.

7. The system as defined in claim 6 wherein said floor is surrounded by an annular shoulder which extends around said end of said electrode.

8. A dust recovery system for an electrode of an analytical resistance furnace comprising:
   an analytical furnace including a chamber for housing an upper electrode;
   an upper electrode positioned in said chamber and having a crucible-receiving furnace with a contact for engaging one end of a resistive crucible, said upper electrode having an end spaced from said contact with a plurality of grooves formed therein;
   a lower electrode for supporting an opposite end of a crucible within said furnace of said upper electrode; and
   a manifold fitted over said end of said upper electrode to define a dust recovery plenum surrounding said plurality of grooves in said upper electrode, said dust recovery plenum including an outlet for coupling to a vacuum source to remove debris from said electrode, wherein said manifold includes an annular floor which engages an end surface of said electrode and wherein said floor is surrounded by an annular shoulder which extends around said end of said electrode and wherein said end of said upper electrode is generally circular and said annular shoulder includes a vertically extending annular wall having a diameter greater than the diameter of said end of said upper electrode and a horizontal annular lip spaced from said annular floor and having a diameter to receive said end of said upper electrode in closely spaced relationship.

9. The system as defined in claim 8 wherein said manifold further includes a slot formed in said shoulder for receiving an analytical gas outlet associated with said electrode.

10. The system as defined in claim 9 wherein said manifold includes a tangentially extending projection with said outlet formed therein and communicating with said plenum defined by the space between said shoulder and said electrode.

11. The system as defined in claim 10 wherein said manifold is fabricated of a polymeric material.

12. The system as defined in claim 11 wherein said polymeric material is polyether ether ketone.

13. The system as defined in claim 12 wherein said manifold includes a plurality of apertures formed in said floor for receiving fasteners for attaching said manifold to said end of said electrode.

14. A dust recovery system for an electrode of an analytical resistance furnace comprising:
   an analytical furnace including a chamber for housing an upper electrode;
   an upper electrode positioned in said chamber and having a cylindrical passageway having a lower end defining a crucible-receiving furnace with a contact for engaging one end of a resistive crucible, said upper electrode having a flange at an end spaced from said contact, said flange having a plurality of radially outwardly extending grooves formed therein;
   a lower electrode for supporting an opposite end of a crucible within said furnace of said upper electrode;
   an air passageway for admitting air to said cylindrical passageway of said upper electrode; and
   a manifold fitted over said flange of said upper electrode to define a dust recovery plenum surrounding said plurality of grooves, said dust recovery plenum including an outlet for coupling to a vacuum source to remove debris from said electrode.

15. The system as defined in claim 14 wherein said grooves are curved.

16. The system as defined in claim 15 wherein said grooves are helical.

17. The system as defined in claim 16 wherein said grooves increase in size in a radially outward direction.

18. The system as defined in claim 17 wherein said grooves extend tangentially to said plenum.

19. The system as defined in claim 14 wherein said manifold includes an annular floor which engages an end surface of said flange.

20. The system as defined in claim 19 wherein said floor is surrounded by an annular shoulder which extends around said flange of said upper electrode.

21. The system as defined in claim 20 wherein said flange of said upper electrode is generally circular and said annular shoulder includes a vertically extending annular wall having a diameter greater than the diameter of said flange of said upper electrode and a horizontal annular lip spaced from said annular floor and having a diameter to receive said flange of said upper electrode in closely spaced relationship.

22. The system as defined in claim 21 wherein said manifold further includes a slot formed in said shoulder for receiving an analytical gas outlet associated with said electrode.

23. The system as defined in claim 22 wherein said manifold includes a tangentially extending projection with said outlet formed therein and communicating with said plenum defined by the space between said shoulder and said electrode.

24. The system as defined in claim 23 wherein said manifold is fabricated of a polymeric material.

* * * * *